United States Patent [19]

Hanessian

[11] 4,066,753
[45] Jan. 3, 1978

[54] NEOMYCIN AND PAROMOMYCIN DERIVATIVES

[75] Inventor: Stephen Hanessian, Beaconsfield, Canada

[73] Assignee: Canadian Patents and Development Limited, Ottawa, Canada

[21] Appl. No.: 690,733

[22] Filed: May 27, 1976

[51] Int. Cl.² .................. A61K 31/71; C07H 15/22
[52] U.S. Cl. ........................ 424/181; 195/31 R; 195/31 P; 424/180; 536/12; 536/17
[58] Field of Search ............ 536/12, 17; 424/181, 424/180

[56] References Cited

U.S. PATENT DOCUMENTS

| | | | |
|---|---|---|---|
| 3,860,574 | 1/1975 | Naito et al. | 536/12 |
| 3,897,412 | 7/1975 | Naito et al. | 536/17 |
| 3,923,783 | 12/1975 | Naito et al. | 536/17 |
| 3,956,274 | 5/1976 | Umezawa et al. | 536/17 |

*Primary Examiner*—Johnnie R. Brown

[57] ABSTRACT

The invention relates to novel neomycin and paromomycin derivatives having antibiotic activity. The derivatives have the formula:

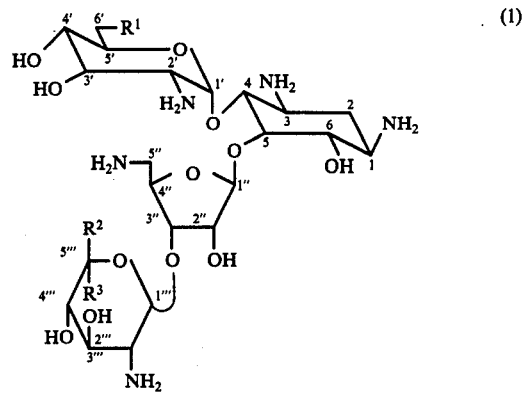

wherein R' is —NH$_2$ or —OH, either R$^2$ or R$^3$ is —CH$_2$NH$_2$ and the other is hydrogen, and in addition non-toxic pharmaceutically acid addition salts of these compounds can be used.

11 Claims, No Drawings

NEOMYCIN AND PAROMOMYCIN DERIVATIVES

BACKGROUND OF THE INVENTION

1. Field of the Invention

This invention relates to derivatives of neomycin and paromomycin having antibiotic activity, and to methods of making said derivatives.

2. Description of the Prior Art

Neomycin and paromomycin are commercially important aminoglycoside antibiotics, and their structures, preparation and properties are described in the Merck Index, 8th Edition, pages 723-724 and 784, respectively. A drawback to their use, however, is their enzymatic inactivation by a phosphotransferase enzyme present in "resistant" gram-negative bacteria, such as certain strains of *E. Coli* and *P. Aeruginosa.*

SUMMARY OF THE INVENTION

It is an object of the present invention to provide novel neomycin and paromomycin derivatives having antibiotic activity, and methods of preparing the same.

According to one aspect of the invention there is provided a compound having the formula:

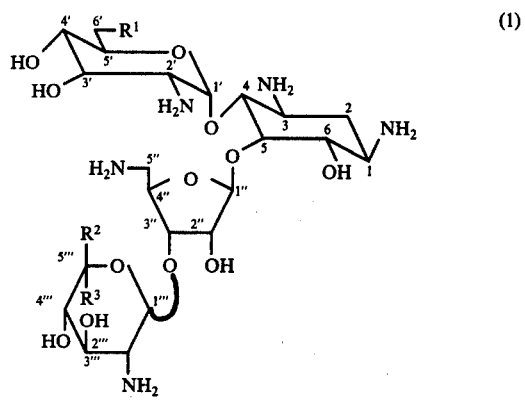

(1)

wherein $R^1$ is $-NH_2$ or $-OH$, either $R^2$ or $R^3$ is $-CH_2NH_2$ and the other is hydrogen; or a non-toxic parmaceutically acceptable acid addition salt thereof.

DETAILED DESCRIPTION OF PREFERRED EMBODIMENTS (A) Preparation of 5''-amino-5''-deoxyneomycin One method of preparing 5''-Amino-5''-deoxyneomycin is from neomycion by protection of the amino groups of neomycin, followed by selective, sequential bromination and amination of the 5'' position. Removal of the protecting groups then affords the desired compound.

This route is illustrated by Scheme I below, in which the starting material is neomycin B and the product is 5''-amino-5''-deoxyneomycin B.

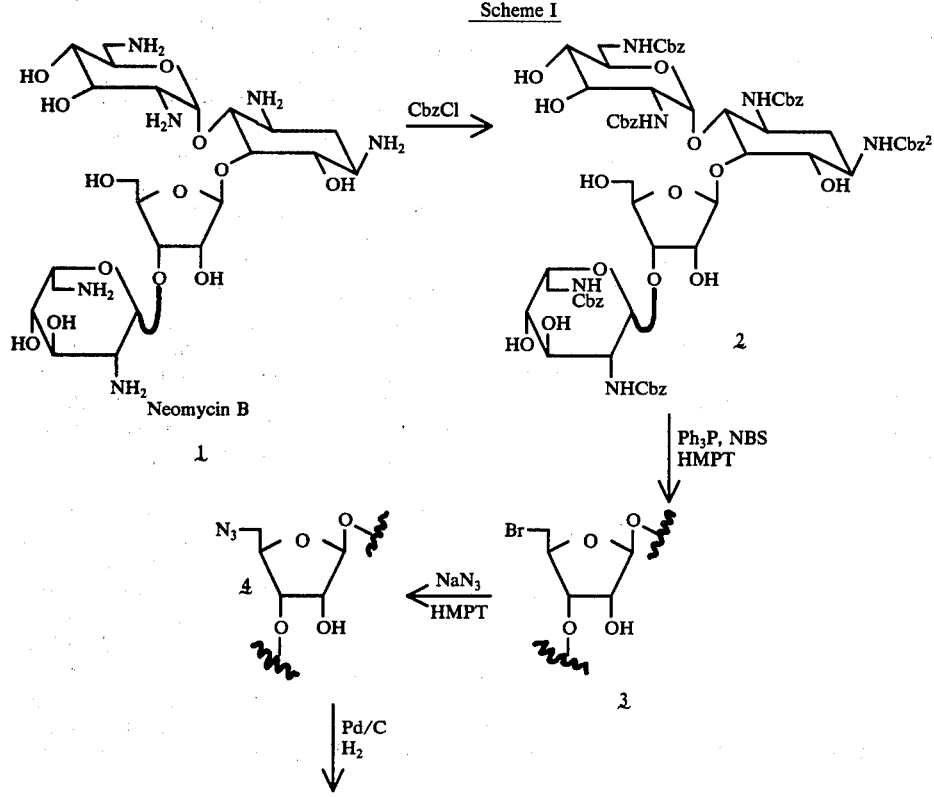

Scheme I

-continued

Scheme I

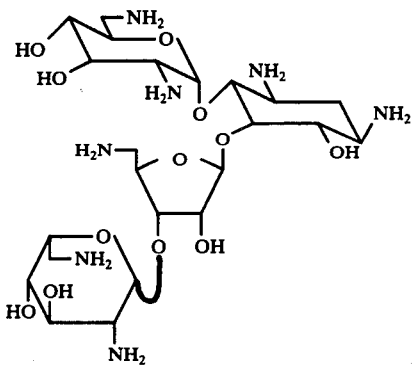

5''-Amino-5''-deoxyneomycin B.

NB. Throughout this specification:
  CbzCl represents benzyloxycarbonyl chloride
  NBS represents N-bromosuccinimide,
  HMPT represents hexamethylphosphoramide,
  AcOH represents acetic acid, and
  PhCHO represents benzaldehyde.

In Scheme I, neomycin B (compound 1) is reacted in a first step with benzyloxycarbonyl chloride in order to N-protect all of the —NH$_2$ groups. This results in the formation of compound 2 which is hexa-N-benzyloxycarbonylneomycin B. In this reaction, a salt of neomycin B, such as the sulfate, may be used instead of the free base. The reaction is usually conducted in an aqueous solution containing sodium carbonate at 0° C with vigorous stirring. The product is then extracted from the aqueous solution and is converted into compound 3 (5''-bromo-5''-deoxy-hexa-N-benzyloxycarbonylneomycin B) by treatment with a brominating agent, such as N-bromosuccinimide preferably in hexamethylphosphoramide, in the presence of triphenylphosphine. In this manner, the —OH group in the 5''-position is replaced by a bromine atom, the other groups remaining unchanged.

The resulting compound 3 is converted into compound 4 (5''-azido-5''-deoxy-hexa-N-benzyloxycarbonylneomycin B) by treatment with sodium azide, preferably at 0° C in hexamethylphosphoramide. This reaction replaces the —Br atom in the 5''-position by an —N$_3$ group.

The final step is the preparation of 5''-amino-5''-deoxyneomycin B (compound 5) by the hydrogenation of compound 4 in the presence of palladium hydroxide-on-carbon as catalyst in a suitable medium such as a mixture of dioxane and methanol.

A modification of the above scheme involves the direct preparation of compound 4 from compound 2 i.e. without the intermediate isolation of compond 3. This is accomplished by treatment of compound 2 with N-bromosuccinimide in the presence of triphenylphosphine, as described before, followed by destruction of excess N-bromosuccinimide-triphenylphosphine reagent with a suitable reagent such as methanol and the addition of sodium azide. The mixture is heated for a period of several hours and can then be poured into ice water to give the desired product (compound 4).

Scheme I can equally well be applied to neomycin C as the starting material, in which case the product is 5''-amino-5''-deoxyneomycin C, or to a mixture of neomycin B and neomycin C in which case the product is a mixture of the B and C derivatives.

A second method of preparing 5''-amino-5''-deoxy neomycin is from paromomycin by protection of the —NH$_2$ groups, followed by selective, sequential bromination and amination of the 5''- and 6'-positions. Removal of the protecting groups then affords the desired compound. This route is illustrated by Scheme II below and is similar to Scheme I except that the —OH group in the 6'-position of paromomycin reacts in the same way as the —OH group in the 5''-position and is thus converted into an —NH$_2$ group to yield a neomycin derivative.

Scheme II

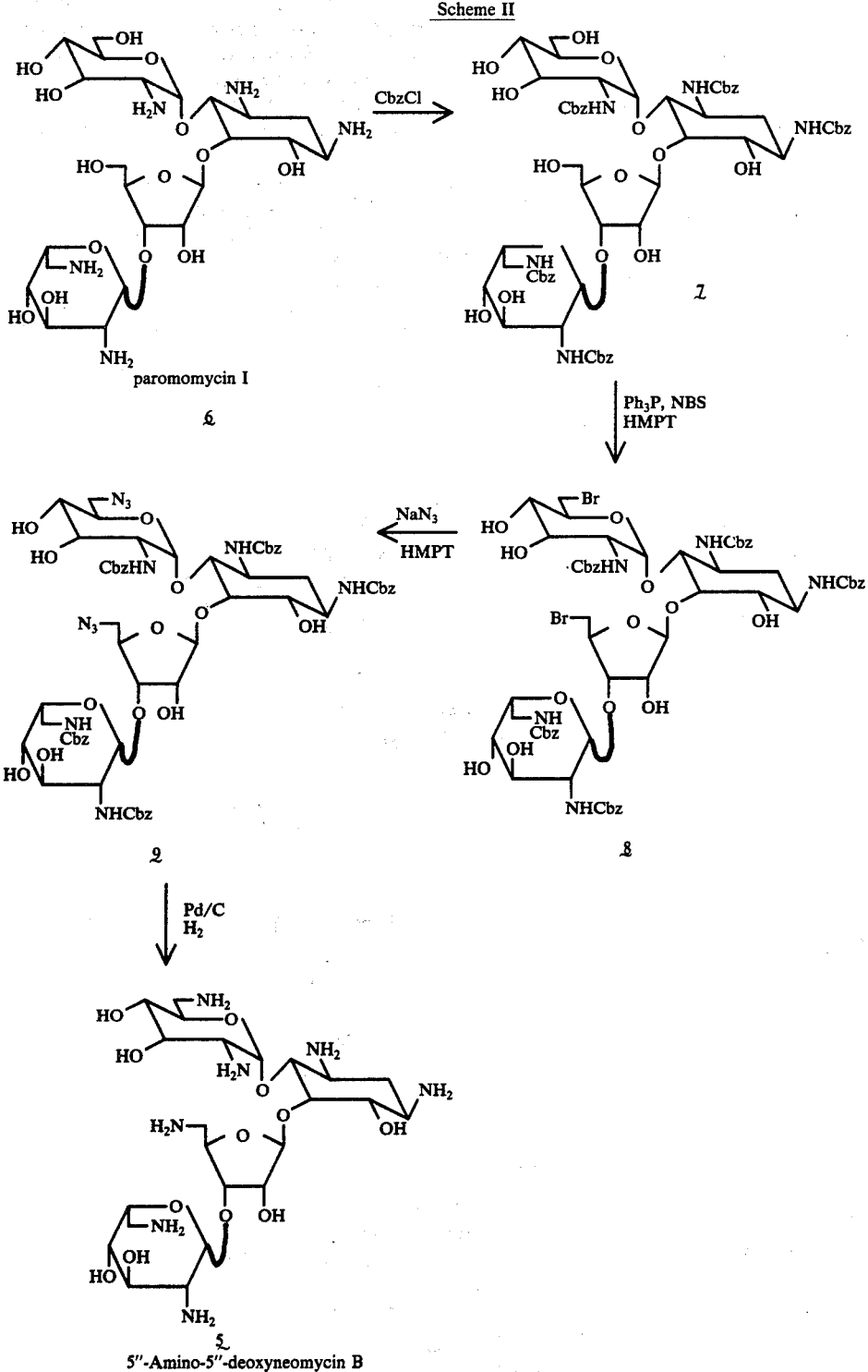

5''-Amino-5''-deoxyneomycin B

Paromomycin I is converted into 5'',6'-dibromo-5'',6'-dideoxy-penta-N-benzyloxycarbonyl-paromomycin I (compound 8) via penta-N-benzyloxycarbonyl-paromomycin I (compound 7).

Alternatively, a solution containing penta-N-benzyloxycarbonylparomomycin I (compound 7) is obtained as disclosed in Tetrahedron Letters 4009, 1974 (T. Takamoto and S. Hanessian). To this solution is added N-bromosuccinimide and triphenylphosphine in hexamethylphosphoramide and the solution is heated and stirred and the product (compound 8) extracted.

The product is then used in the preparation of 5'',6'-diazido-5'',6'-dideoxy-penta-N-benzyloxycarbonyl-paromomycin I, as follows. The said compound of the preceding step (compound 8) is heated with sodium azide in hexamethylphosphoramide. The solution is then poured into ice-water, and the product (compound 9) is extracted. Compound 9 can also be prepared from penta-N-benzyloxycarbonylparomomycin I (compound 7) without the intermediate step of isolation of the dibromo derivative (compound 8) as described in relation to Scheme I above.

5"-Amino-5"-deoxyneomycin B (compound 5) is then prepared from the resulting compound 9 by hydrogenation as in Scheme I.

Scheme II is also applicable to paromomycin II as starting material, in which case 5"-amino-5"-deoxyneomycin C is produced, or a mixture of paromomycin I and paromomycin II can be used as the starting material, in which case a mixture of I and II derivatives is obtained.

(B) Preparation of 5"-Amino-5"-deoxyparomomycin

5"-Amino-5"-deoxyparomomycin can be prepared from paromomycin by protection of the amino groups and a pair of the hydroxyl groups, followed by sequential bromination and amination of the 5"-position. Removal of the protecting groups affords the desired compound. This route is illustrated by Scheme III below.

Takamoto and S. Hanessian). A solution containing this compound, triphenylphosphine and N-bromosuccinimide in hexamethylphosphoramide is heated, methanol is added, followed by sodium azide and the solution is heated again resulting in the formation of the said compound 12. This compound can also be prepared in a two-step sequence from compound 2 by bromination to give the 5"-bromo derivative (compound 11) and isolation of this derivative followed by displacement of the bromine atom with an azide group.

5"-amino-5"-deoxyparomomycin I (compound 14) is then obtained from compound 12 by reaction with acetic acid in solution to remove the group protecting the 4'- and 6'-positions to give compound 13, followed by hydrogenation as in Schemes I and II above.

Scheme III

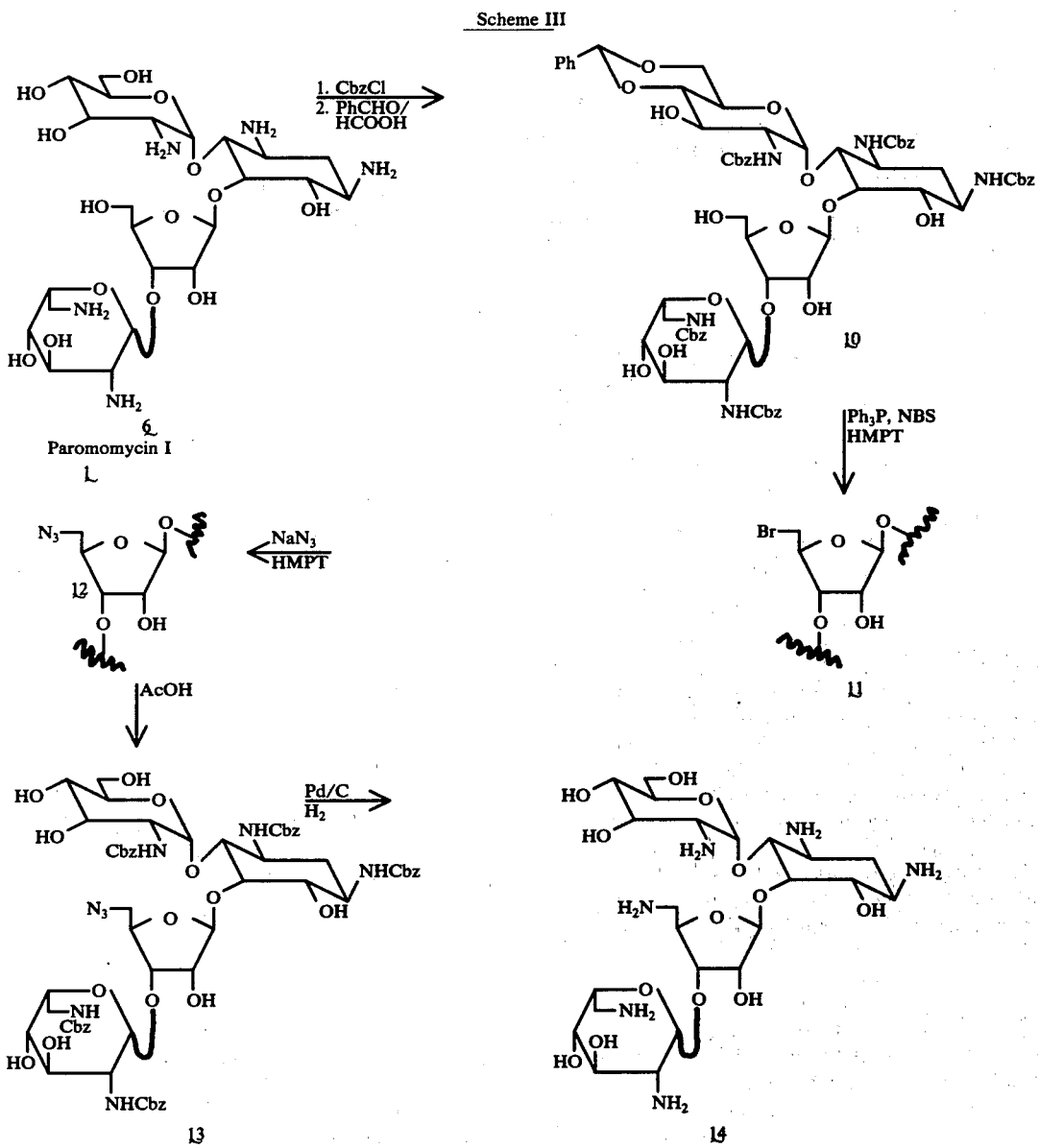

Paromomycin I (compound 6) is converted to 5"-azido-4',6'-O-benzylidene-5"-deoxyparamycin I (compound 12) by first obtaining 4',6'-O-benzylidene-penta-N-benzyloxycarbonylparomomycin I (compound 10) as disclosed in Tetrahedron Letters 4009, 1974 (T.

(C) Antibacterial activity of
5''-amino-5''-deoxyneomycin and
5''-amino-5''-deoxyparomomycin Both the neomycin B derivatives and the paromomycin I derivative show broad spectrum antibacterial activity, including activity against *E. Coli* that is resistant to neomycin and paromomycin.

The antibacterial activity is shown in the following Tables.

| IN VITRO Antibacterial Activity of 5''-amino-5''-deoxyneomycin B (MIC µg/ml) | | |
|---|---|---|
| | Compound | |
| Strain | Neomycin B | 5''-Amino-5''-deoxyneomycin B |
| S. pyogenes S B352 | < 0.2 | < 0.1 |
| S. pyogenes R 353 | < 0.2 | < 0.1 |
| S. fecalis 353 | 0.8 | 0.8 |
| E. Coli 198 (ATCC 1/229) | 0.8 | 0.8 |
| A. aerogenes 357 | < 0.2 | 0.8 |
| S. pullorum 358 | < 0.2 | 0.4 |
| P. aeruginosa 359 | 0.8 | 1.6 |
| Pr. mirabilis 360 | 0.4 | 0.8 |
| Pr. vulgaris 316 | < 0.2 | 0.8 |
| Kl. pneumoniae 855 (ATCC 10081) | < 0.2 | 0.4 |
| S. marcesceus 854 (ATCC → 103) | < 0.2 | 0.4 |

| IN VITRO Antibacterial Activity of 5''-Amino-5''-deoxyneomycin B against some Resistant organisms (MIC µg/ml) | | | | |
|---|---|---|---|---|
| | Compound | | | |
| Strain | Gentamycin | Kanamycin | Neomycin | 5''-Amino analog |
| P. aeruginosa 87442 | < 0.2 | 0.8 | < 0.2 | 0.8 |
| P. aeruginosa 377 | < 0.2 | 3.2 | 0.4 | 1.6 |
| E. coli B989 | < 0.2 | 100 | 1.6 | 1.6 |
| E. coli B1002 | < 0.2 | < 100 | 50 | 3.2 |

| Acute Toxicity Data | |
|---|---|
| Neomycin B LD$_{50}$ | 40–60 mg/Kg in mice (i.v). |
| 5''-Amino-5''-deoxyneomycin B LD$_{50}$ | 60–80 mg/Kg in mice (i.v). |

| IN VITRO Antibacterial Activity of 5''-amino-5''-deoxyparomomycin I, (MIC, µg/ml) | | |
|---|---|---|
| | Compound | |
| Strain | Paromomycin | 5''-amino analog |
| S. pyogenes S | < 0.2 | < 0.2 |
| S. pyogenes R | < 0.2 | 0.4 |
| S. fecalis | 1.6 | 6.4 |
| E. coli 198 | 0.4 | 6.4 |
| A. aerogenes | > 0.2 | 1.6 |
| S. pullorm | > 0.2 | 0.8 |
| P. aeruginosa | 0.8 | 12.5 |
| P. mirabilis | > 0.2 | 1.6 |
| K. pneumoniae | > 0.2 | 0.8 |
| S. marcesceus | 0.4 | 0.8 |
| E. coli B996* | > 100 | 12.5 |

*resistant to Kanamycin and paromomycin

NOTE
In the Tables above MIC stands for minimum inhibitory concentration and the results were obtained by providing halving dilutions of the test compound in nutrient broth (concentrations usually range from 1/10,000 to 1/320,000). These solutions are inoculated with the test organism, incubated for 24 hours at 37° C and then examined for the presence of growth. A test compound found to have a minimum inhibitory concentration (MIC) of 1/160,000 is generally considered as a lead.

The results above show that 5''-amino-5''-deoxyneomycin B and 5''-amino-5''-deoxyparomomycin I are particularly effective against strains of *E. Coli* and *P. Aeruginosa* which are resistant to neomycin B and paromomycin I.

The novel compounds can be used as antibiotics to treat similar diseases in a similar way to the parent compounds neomycin and paromomycin, the dosages being similar to those of neomycin and paromomycin. The usual solvents, diluents and carriers can be used in the preparation of suitable doses. The neomycin derivatives are often used topically in cream or ointment form and the paromomycin derivatives are useful for the treatment of amebic disentery, shigellosis, and salmonellosis.

Thus, the compounds of this invention are valuable as anti-bacterial agents (especially for the supression of intestinal bacteria), nutritional supplements in animal feeds, therapeutic agents in poultry and animals, including man, and are especially valuable in the treatment of infectious diseases caused by Gram-positive and Gram-negative bacteria. They can be used in the treatment of systemic bacterial infections when administered parenterally in the dosage range of about 250 mg. to about 3000 mg. per day in divided doses three or four times a day. Generally the compounds are effective when administered at a dosage of about 5.0 to 7.5 mg/Kg of body weight every 12 hours.

They may also be used for topical therapy, typically in an amount of about 0.5% in a cream or ointment, the neomycin derivatives being particularly useful in this form.

In addition to the compounds themselves, pharmaceutically acceptable salts thereof can be formed and used in the usual way. For example, the mono-, di-, tri-, tetra-, penta- or hexa-salts (where appropriate) can be formed by the interaction of one mole of the stated compounds with 1 to 6 moles of a pharmaceutically acceptable acid, eg. citric acid, ascorbic acid, acetic acid, hydrochloric acid, sulfuric acid, maleic acid, nitric acid, phosphoric acid, hydrobromic acid, and other acids commonly used to form the salts of basic pharmaceuticals.

The following Examples illustrate certain aspects of the invention but are not intended to limit the scope of the invention as defined by the appended claims.

EXAMPLE 1

Preparation of 5''-Amino-5''-deoxyneomycin B from Neomycin B a. Hexa-N-benzyloxycarbonylneomycin B (compound 2):

An amount (11.44 g) of neomycin sulfate (a mixture of B and C components, but rich in the former) was dissolved in 150 ml of water and 25 g of sodium carbonate was added. The solution was diluted with methanol (200 ml), cooled to 0°, and treated dropwise with 25 ml of benzyloxycarbonyl chloride, with rigorous stirring. After 4 h, the mixture was diluted with ice-water, stirred for 1 h, and the supernatent liquid was decanted from a syrupy residue. The latter was repeatedly triturated with petroleum ether (b.p. 30°–60°), then with water. The residue was dissolved in a mixture of chloroform and methanol (1:1), the solution was filtered, and the filtrate was evaporated to a colorless foam. Trituration with petroleum ether afforded a colorless amorphous powder, which was dried under vacuum. Yield, 16.06 g (89%).

A portion (4.76 g) of this product was chromatographed on a column containing silica gel (50 g/gm of product). Elution with chloroform (100 ml) followed by a mixture of chloroform-ethyl acetate-methanol, 20:5:2, afforded 3.67 g of chromatographically pure hexa-N-benzyloxycarbonylneomycin B, m.p. 116°–120°; $[\alpha]_D^{27}$ + 32.9° (c 0.54, chloroform).

b. 5''-Bromo-5''-deoxy-hexa-N-benzyloxycarbonyl-neomycin B (compound 3):

The preceding compound (2.23 g, 1.99 mmole, previously dried by codistillation with pyridine, then toluene), was dissolved in 65 ml of hexamethylphosphoramide and the solution was treated with 1.35 g (5.16 mmoles) of triphenylphosphine. The solution was cooled, and 0.89 g (5.00 mmoles) of N-bromosuccinimide was added in small portions with stirring. After heating at 55° for 4 h, methanol was added to decompose excess reagent, the solution was evaporated and the residual solvent was distilled at 70° under vacuum. The resulting residue was triturated with cold water, and the solid so obtained was washed successively with water and petroleum ether (b.p. 30°–60°). The product was purified by chromatography on silica gel using chloroform-ethyl-acetate and methanol (20:5:2) as eluent. The desired compound was obtained as a colorless amorphous solid; (2.41, 91%) mp 124°–126°; $[\alpha]_D^{27}$ + 22.9° (c 0.52, Chf); $R_f$(Chf. EtOAc-MeOH, 20:5:3) 0.37.

Calculated for $C_{71}H_{81}O_{24}N_8Br \cdot 2H_2O$. C, 56.16; H, 5.38; N, 5.53. Found C, 55.92; H, 5.56; N, 5.49.

The reaction was also conducted in DMF as solvent and the product was obtained in 53% yield.

c. 5''-Azido-5''-deoxy-hexa-N-benzyloxycarbonyl-neomycin B (compound 4);

A solution containing 1.84 g of the preceding compound in 30 ml of hexamethylphosphoramide was treated with 2.23 g of sodium azide and the mixture was heated at 55° for 4–6 h. The mixture was cooled to 0°, ice water (800 ml) was added, and the precipitate was filtered and washed with water. Chromatography on silica gel as previously described eliminated trace amounts of impurities and afforded the desired compound, as a chromatographically homogeneous amorphous solid 1.49 g (82%); mp 119°–121°; $[\alpha]_D^{27}$ + 30° (c 1.09, Chf); i.r. data, $\lambda_{max}$ 3450 cm$^{-1}$ – 3300 cm$^{-1}$ (OH, NH); 2100 cm$^{-1}$(N$_3$); 1680 cm$^{-1}$ (C=O).

The product was readily distinguished from its precursor on thin layer chromatograms and was suitable for use in the next step.

d. 5''-Amino-5''-deoxyneomycin B (compound 5);

The 5''-azido derivative (1.98 g) was dissolved in 50 ml of dioxane and 25 ml of methanol, and 10 ml of N hydrochloric acid was added. The solution was hydrogenated in presence of 1.50 g of 20% palladium hydroxide-on-carbon catalyst (W. Pearlman, Tetrahedron Letters, 1663, 1967). After 6 h the catalyst was filtered, and the filtrate was evaporated to give a pale yellow syrup. The latter was dissolved in water (5 ml) and ethanol was added with stirring to precipitate the desired compound as its colorless amorphous hydrochloride salt. Yield 1.02 g (85%) of 5''-amino-5-Deoxymneomycin. HCl; mp 205°–210° (dec.); $[\alpha]_D^{27}$ + 44.7° (c 0.94 H$_2$O).

$R_f$ (paper Whatman No. 1, n-Propanol-pyridine. AcOHH$_2$O: 15:10:3:12), 9.2 cm from point of application, after 21 h of elution; for neomycin B; 5.2 cm $R_f$ (silica gel, chloroform-methanol-NH$_4$OH, 1:3:2), 0.16; for neomycin B, 0.20.

The structure of the product was further confirmed by chemical degradation, by $^{13}$C magnetic resonance spectroscopy, and by high resolution mass spectrometry of its N-acetyl-O-trimethylsilyl derivative.

Preparation of 5''-amino-5''-deoxyneomycin B from Paromomycin I, 6.

a. 5''-6'-Dibromo-5'',6'-dideoxy-penta-N-benzyloxycarbonylparomomycin I, 7:

A solution containing 0.215 g (0.16 mmole) of penta-N-benzyloxycarbonylparomomycin I (T. Takamoto and S. Hanessian, Tetrahedron Letters 4009, 1974), 01.68 g (0.64 mmole) of triphenylphosphine, and 0.11 g (0.63 mmole) of N-bromosuccinimide, in 10 ml of hexamethylphosphoramide is heated with stirring at 55° for 5 h. After usual workup (see above), the title compound is isolated by column chromatography, yield 0.166 g (68%) of an amorphous colorless solid, mp 124°–126°; $[\alpha]_D^{27}$ + 39.1 (c 0.92, CHf);

$R_f$ (silica gel, Chf-EtOAc-MeOH, 20:5:3) 0.43 The product was used as such in the following step.

b. 5'',6'-Diazido-5''-6'-dideoxy-penta-N-benzyloxycarbonyl-paromomycin I, 8:

The preceding compound (0.160 g) and 0.160 of sodium azide are heated at 55° for 4 h in 10 ml of hexamethylphosphoramide. The solution is poured into ice-water, the precipitate is filtered, washed with water, then petroleum ether and dried. Yield 0.121 g (82%) of the title compound, mp 97°–100°. $[\alpha]_D^{27}$ + 43.9 g (c 2.32 Chf)

Anal. Calculated for $C_{63}H_{73}O_{22}N_{11}$: C, 56.62; H 5.51; N, 11.53. Found C, 56.80; H, 5,69; N, 11.85.

The above compound could also be prepared from penta-N-benzyloxycarbonylparomomycin I, 9, without isolation of the intermediate dibromo derivative 7; yield 80%.

c. 5''-Amino-5''-deoxyneomycin B, 5:

Hydrogenation of the preceding derivative (0.14 g) as previously described, gave 0.08 g (87.6%) of 5''-amino-5''-deoxy neomycin B.HCl, mp 205°–210° (dec.); $[\alpha]_D^{27}$ + 45 (c 1.04, H$_2$O.

EXAMPLE 2

Preparation of 5''-Amino-5''-deoxyneomycin B from neomycin B Employing Direct Preparation of 5''-azido-5''-deoxy-hexa-N-carbobenzyloxyneomycin B (compound 4) from hexa-N-benzyloxycarbonylneomycin B (compound 2)

Hexa-N-benzyloxycarbonylneomycin B was prepared as in Example I. A solution containing 0.52 g (0.36 mmole) of the resulting hexa-N-benzyloxycarbonylneomycin B, and 0.241 g (0.92 mmole) of triphenylphosphine, in 20 ml of hexamethylphosphoramide was cooled to 0° and treated with N-bromosuccinimide as described in Example 1. After stirring for 4 h at 55°, excess reagent was destroyed by adding methanol (1 ml), and then 0.6 g of sodium azide was added. The mixture was heated at 55° for 4–6 h, and then poured into ice-water, to give the 5''-azido-5''-deoxy-hexa-N-carbobenzyloxyneomycin B. Purification by column chromatography afforded 0.38 g (73%) of this compound, which was then hydrogenated as in Example I to yield 5''-amino-5''-deoxyneomycin B.

EXAMPLE 3

Preparation of 5''-Amino-5''-deoxyparomomycin I (compound 14)

(a) 5''-Azido-4',6'-O-benzylidene-5''-deoxyparomomycin I (compound 12):

A solution containing 0.49 g (0.35 mmole) of 4',6'-O-benzylideneparomomycin (prepared as in article by T.

Takamoto and S. Hanessian, Tetrahedron Letters, 4009, 1974), 0.235 g (0.89 mmole) of triphenylphosphine, and 0.157 g (0.88 mmole) of N-bromosuccinimide, in 20 ml of hexamethylphosphoramide was heated at 55° for 4 hours as previously described. Methanol was added, followed by sodium azide and the solution was heated at 55° again, to give 0.35 g (76%) of compound 12 as an amorphous, chromatographically homogeneous solid, mp 123°–125°; $[\alpha]_D^{27} + 37°$ (c 0.92, Chf);

i.r. data: $_{max}$ 3400 cm$^{-1}$ (OH, NH); 2100 cm$^{-1}$ (N$_3$), 1700 cm$^{-1}$ (C=O)

The product was suitable for use in the next step. It was also prepared in a two step sequence from compound 2 by bromination to give the 5″-bromo derivative (compound 11), followed by displacement with an azide ion.

b. 5″-Amino-5″-deoxyparomomycin I (compound 14):

A solution containing 0.95 g of the preceding product was dissolved in 20 ml of 80% acetic acid and the solution was left at room temperature for 48 hours. Evaporation gave a residue that was chromatographed on silica gel (chloroform-EtOAcMeOH, 20:5:2), to give 0.7 g (79%) of 5″-azido-5″-deoxy-penta-N-benzyloxycarbonylparomomycin I, 5, as a colorless solid, mp 118°–120°; $[\alpha]_D^{27} + 40°$ (c 1.01, Chf)

Anal, Calculated for $C_{63}H_{74}O_{23}N_8$: C, 57.70; H, 5.69; N, 8.54. Found C, 57.41; H, 5.91; N, 8.21.

A portion of the above product (0.17 g) was hydrogenated as previously described to give 5″-amino-5″-deoxyparomomycin I hydrochloride (0.07 g, 70%); mp 200°–202° (dec.); $[\alpha]_D + 42.2°$ (c 0.57, H$_2$O)

R$_f$ (silica gel, Chf-MeOH-NH$_4$OH 1:3:2), 0.26; for paromomycin I, 0.32

R$_f$ (paper chromatography, n-Propanol-pyridine-AcOH-H$_2$O, 15:10:3:12), 10.4 cm from point of application, in 21 h; for paromomycin 15.1 cm.

The structure of the product was also substantiated by chemical degradation, by $^{13}$C magnetic resonance spectroscopy, and by high resolution mass spectrometry.

I claim:

1. A compound having the formula

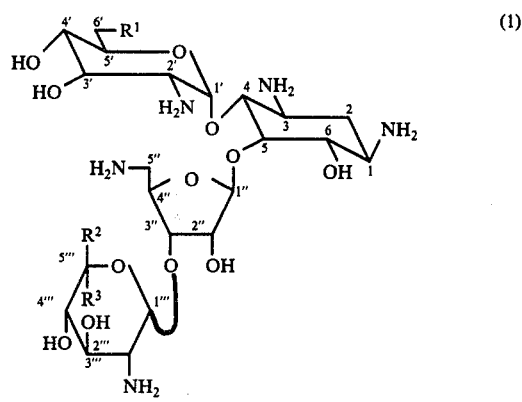

wherein R$^1$ is selected from —NH$_2$ and —OH, one of R$^2$ and R$^3$ is —CH$_2$NH$_2$ and the other is hydrogen; or a non-toxic pharmaceutically acceptable acid addition salt thereof.

2. A compound according to claim 1 wherein said salt is selected from the group consisting of the citric acid, ascorbic acid, acetic acid, hydrochloric acid, sulfuric acid, maleic acid, nitric acid, phosphoric acid and hydrobromic acid salts.

3. A compound according to claim 1 wherein R$^1$ is —NH$_2$, R$^2$ is H and R$^3$ is —CH$_2$NH$_2$; or a non-toxic pharmaceutically acceptable acid addition salt thereof.

4. A compound according to claim 3 wherein said salt is selected from the group consisting of the citric acid, ascorbic acid, acetic acid, hydrochloric acid, sulfuric acid, maleic acid, nitric acid, phosphoric acid and hydrobromic acid salts.

5. A compound according to claim 1 wherein R$^1$ is —OH, R$^2$ is H and R$^3$ is —CH$_2$NH$_2$; or a non-toxic pharmaceutically acceptable acid addition salt thereof.

6. A compound according to claim 5 wherein said salt is selected from the group consisting of the citric acid, ascorbic acid, acetic acid, hydrochloric acid, sulfuric acid, maleic acid, nitric acid, phosphoric acid and hydrobromic acid salts.

7. An antibiotic composition comprising as an active ingredient a compound according to claim 1 together with a pharmaceutically acceptable solvent, diluent or carrier.

8. A composition according to claim 7 wherein the active ingredient is in the form of a salt selected from the group consisting of the citric acid, ascorbic acid, acetic acid, hydrochloric acid, sulfuric acid, maleic acid, nitric acid, phosphoric acid and hydrobromic acid salts.

9. A composition according to claim 7 wherein, in the active ingredient, R$^1$ is —NH$_2$, R$^2$ is H and R$^3$ is —CH$_2$NH$_2$.

10. A composition according to claim 7 wherein, in the active ingredient, R$^1$ is —OH, R$^2$ is H and R$^3$ is —CH$_2$NH$_2$.

11. A method of treating amoebic dysentery in human beings and in animals, which method comprises administering an effective amount of a compound according to claim 1 to the human being or animal.

* * * * *